(12) United States Patent
Fauci et al.

(10) Patent No.: US 7,265,350 B2
(45) Date of Patent: Sep. 4, 2007

(54) INTEGRATED MULTI-SPECTRAL IMAGING SYSTEMS AND METHODS OF TISSUE ANALYSES USING SAME

(75) Inventors: Mark A. Fauci, Patchogue, NY (US); Mihai Dimancescu, Freeport, NY (US)

(73) Assignee: Advanced BioPhotonics, Inc., Bohemia, NY (US)

( * ) Notice: Subject to any disclaimer, the term of this patent is extended or adjusted under 35 U.S.C. 154(b) by 0 days.

(21) Appl. No.: 11/070,925

(22) Filed: Mar. 3, 2005

(65) Prior Publication Data

US 2005/0194537 A1   Sep. 8, 2005

Related U.S. Application Data

(60) Provisional application No. 60/549,728, filed on Mar. 3, 2004, provisional application No. 60/550,209, filed on Mar. 4, 2004.

(51) Int. Cl.
  *G02F 1/01* (2006.01)
(52) U.S. Cl. ...................................................... 250/330
(58) Field of Classification Search ................ 250/330, 250/339.01, 339.05, 353; 356/51; 600/473, 600/476; 348/42, 45
See application file for complete search history.

(56) References Cited

U.S. PATENT DOCUMENTS

| | | | |
|---|---|---|---|
| 5,109,276 A * | 4/1992 | Nudelman et al. ............ 348/47 |
| 5,603,328 A | 2/1997 | Zucker et al. ............... 128/664 |
| 5,910,816 A * | 6/1999 | Fontenot et al. .............. 348/65 |
| 6,181,414 B1 * | 1/2001 | Raz et al. ...................... 356/51 |
| 6,640,130 B1 * | 10/2003 | Freeman et al. ............ 600/474 |
| 6,687,003 B1 * | 2/2004 | Sorensen et al. ........... 356/402 |
| 6,757,422 B1 * | 6/2004 | Suzuki et al. ............... 382/154 |
| 6,937,885 B1 * | 8/2005 | Lewis et al. ................ 600/476 |
| 2002/0071121 A1 * | 6/2002 | Ortyn et al. ................ 356/419 |
| 2003/0025081 A1 * | 2/2003 | Edner et al. ........... 250/339.09 |
| 2003/0067538 A1 * | 4/2003 | Myers ......................... 348/47 |
| 2003/0174315 A1 * | 9/2003 | Byren et al. ............. 356/152.1 |
| 2006/0058611 A1 * | 3/2006 | Descour et al. ............ 600/407 |

* cited by examiner

*Primary Examiner*—David Porta
*Assistant Examiner*—Marcus Taningco
(74) *Attorney, Agent, or Firm*—Mayer & Williams PC; Karin L Williams, Esq.

(57) ABSTRACT

A system is provided utilizing sensors tuned to multiple wavelength spectra for evaluating and imaging an object being monitored. The system includes, among other things, an assembly for splitting a photon beam emitted from an object being monitored into multiple incident rays of different wavelength spectra. A plurality of detectors may be provided, each being tuned to a specific wavelength spectrum of the respective incident ray it is collecting, for converting, into electronic signals, data correlated from the respective incident ray. A processor may be used for generating discrete image data from the electronic signals of each respective incident ray for subsequent display as individual images, or as an integrated multi-spectral image on a display screen. A method for analyzing tissue characteristics is also provided.

6 Claims, 6 Drawing Sheets

INTEGRATED MULTI-SPECTRAL IMAGING SYSTEMS AND METHODS OF TISSUE ANALYSES USING SAME

RELATED U.S. APPLICATIONS

The present application claims priority to U.S. application Ser. Nos. 60/549,728, filed Mar. 3, 2004, and 60/550,209, filed Mar. 4, 2004, both of which are hereby incorporated herein by reference.

TECHNICAL FIELD

The present invention relates to multiple band imaging systems, and more specifically, to multi-band systems and to methods for generating images through the integration of multiple spectra of lights from an object being monitored or observed.

BACKGROUND ART

The concept of infrared imaging for biomedical applications has been explored for some time. The early technology used, unfortunately, had neither the sensitivity, resolution nor speed to be of substantial value. Infrared imaging has now advanced to where it is being used for a range of applications in medicine, and has multiple advantages over conventional medical imaging techniques, including, low cost, no ionizing radiation and no need for contrasting agents. However, these medical imaging systems are limited to collecting and displaying tissue physiology in a single band (i.e., wavelength spectrum) of emission. They display only information pertaining to, for instance, the infrared flux at a single band but cannot display the same image in the visible band or in multiple infrared bands.

There are commercially available systems, at the present time, that permit analysis of multiple bands of light. Spectrophotometric methods are being used to non-invasively monitor oxygen saturation, glucose levels, and the concentration of other blood constituents, for instance, nitrous oxide and carbon dioxide. Spectrophotometric methods are also being used to non-invasively monitor oxidative metabolism of body organs in vivo by using measuring and reference wavelengths in the near-infrared region. Unfortunately, these approaches do not generate a two dimensional (2-D) or three dimensional (3-D) spatial image in connection with the tissue characteristics being monitored or evaluated.

The ability to measure different light spectra can provide unique information about the substances or constituents being monitored. To the extent that an image of the tissue characteristic or the constituents being monitored can be generated, such would provide an added advantage for a variety of medical applications. One approach has been to obtain measurements from an object being imaged using two different detectors at the same time. However, such an approach requires that the angle of view be different for each of the two detecting systems. As a result, the reconstruction, for instance, of a merged image may be difficult.

To avoid the issues associated with different angles of view, single lens systems have been designed to collect different light spectra from the object being observed. However, the single lens solution tend to encounter problems with image degradation, while at the same time being expensive and cost prohibitive.

Alternatively, it is possible, using a filter wheel, to view co-incident but not concurrent images of the same object at different frequencies. An additional limitation to this approach can be the sensitivity range of the single detector that is typically used.

Accordingly, it would be advantageous if multiple bands of lights, such as those in the infrared and visible spectra, being emitted from a target or object being monitored or observed, can be evaluated and analyzed, while images from such spectra can be simultaneously integrated and displayed in real time.

SUMMARY OF THE INVENTION

The present invention provides, in one embodiment, a multi-spectral imaging system having an assembly for splitting a photon beam emitted from an object being monitored into multiple incident rays of different wavelength spectra. In one embodiment, the assembly includes a plurality of mirrors, each designed to reflect an incident ray having photons within a specific wavelength spectrum, while being transparent to photons within different wavelength spectra. The system also includes a plurality of detectors, each being tuned to a specific wavelength spectrum of the respective incident ray it is collecting. The detectors may be designed to convert, into electronic signals, data correlated from the respective incident ray regarding the object being monitored. The detectors, in an embodiment, may include an infrared detector that is a single band detector or a multi-band detector. Such a multi-band detector may be a quantum well infrared photodetector (QWIP). The system may further include a processor for generating discrete image data from the electronic signals of each respective incident ray. The image data regarding the object being monitored may subsequently be displayed as individual images, or as an integrated multi-spectral image on a display screen.

The present invention provides in another embodiment, a multi-spectral imaging system having, among other things, a multi-spectral detector. The multi-spectral detector, in an embodiment, may be designed to receive multiple incident rays, each of a different wavelength spectrum, from an assembly arranged to separate a photon beam emitted from an object being monitored into multiple incident rays of different wavelength spectra. The detectors may also be designed to convert, into electronic signals, data correlated from the incident rays regarding the object being monitored. The system further include a processor for generating discrete image data from the electronic signals of each respective incident ray. The image data in connection with the object may subsequently be displayed as individual images, or as an integrated multi-spectral image on a display screen.

In another embodiment, the present invention provides a multi-spectral imaging system having a lens system through which photon beams within various wavelength spectra that originated from a similar focal point on an object being monitored may be directed. The lens system, in an embodiment, may include a plurality of lenses focused on a similar focal point of the object, and may be used to generate binocular or three dimensional images of the object. The system also includes a plurality of detectors, each being tuned to a specific wavelength spectrum of the respective photon beam it is collecting. Each detector may be constructed to convert, into electronic signals, data correlated from the respective photon beam regarding the object being monitored. The system may further include a processor for generating discrete image data from the electronic signals. The image data in connection with the object may subsequently be displayed as individual images, or as an integrated multi-spectral image on a display screen.

The present invention also provides, in another embodiment, a method for tissue analysis. The method includes splitting a photon beam emitted from a tissue being monitored into multiple incident rays of different wavelength spectra. Next, each of the corresponding incident rays may be collected and data regarding the object being monitored may be correlated from each of the incident rays. Thereafter, the correlated data from each of the incident rays may be converted into electronic signals. Discrete image data may subsequently be generated from the electronic signals to be displayed as individual images, each of a different wavelength spectrum, or as an integrated multi-spectral image. The image data may then be viewed to determined tissue characteristics.

In further embodiment, another method for tissue analysis is provided. The method includes collecting, from a similar focal point of an object being monitored, photon beams of different wavelength spectra. In an embodiment, the photon beams may be collected through the use of multiple lens. Next, data from each of the photon beams may be correlated. The data correlated from each of the photon beams may thereafter be converted into electronic signals. Subsequently, discrete image data may be generated from the electronic signals of each respective photon beam for subsequent display. The image data may then be viewed as individual images or as an integrated multi-spectral image to determine tissue characteristics.

DESCRIPTION OF SPECIFIC EMBODIMENTS

The present invention, in one embodiment, is directed to an integrated multi-spectral imaging system that permits a user to view multiple bands of electromagnetic radiation concurrently as individual images or as a merged or superimposed image. The multi-spectral imaging system of the present invention also provides, in an embodiment, an optical configuration for a variety of applications including, but not limited to, medical imaging.

Figure 1A:
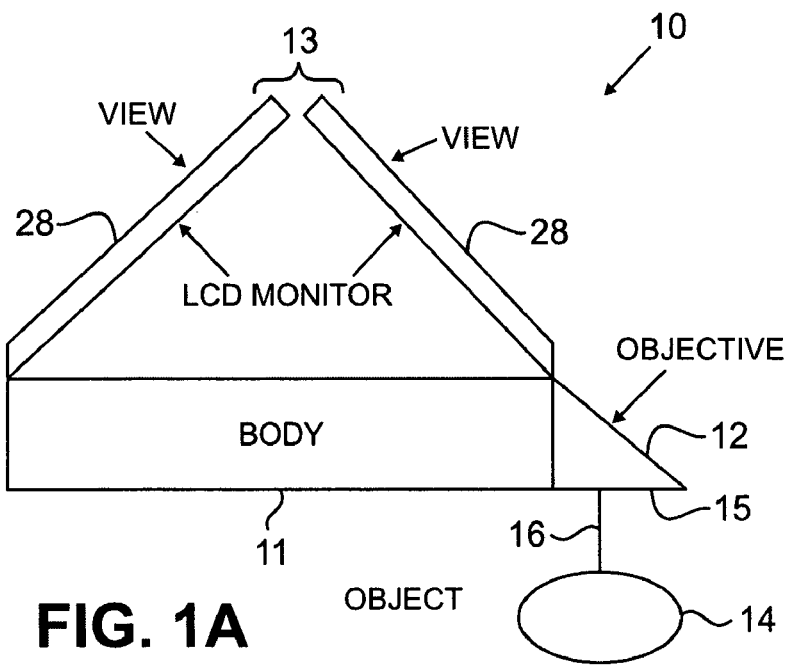
FIGS. 1A-B illustrate, respectively, a perspective view and a side view of an integrated multi-spectral imaging system in accordance with one embodiment of the present invention.
Figure 1B:
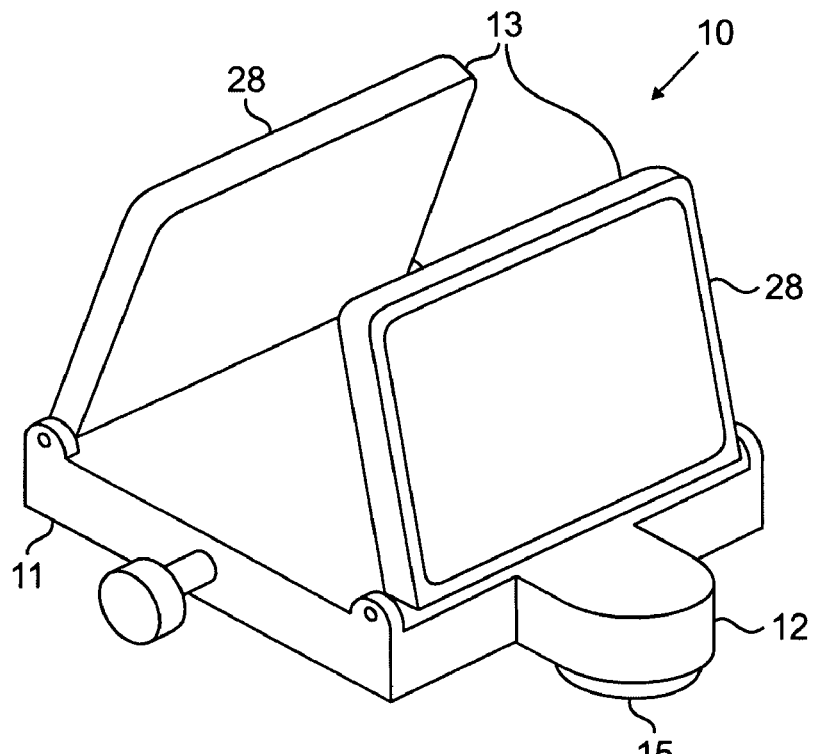

With reference now to FIGS. 1A-B, there is illustrated an integrated multi-spectral imaging system 10 having a body portion 11 within which detection components of the system 10 may be positioned, an objective portion 12 within which integrated optical components may be housed, and an output display portion 13.

As the body portion 11 and the objective portion 12 are designed to house the working components of the integrated multi-spectral imaging system 10, these portions, in one embodiment, may be made from a strong material, such as, a metal, a metal alloy, molded plastic, fiberglass, or a combination thereof. In addition, although illustrated in FIGS. 1A-B with particular designs, it should be appreciated that the body and objective portions, 11 and 12, may be provided with any geometric shape, so long as these portions can accommodate the components for which they have been designed to house.

Figure 2:
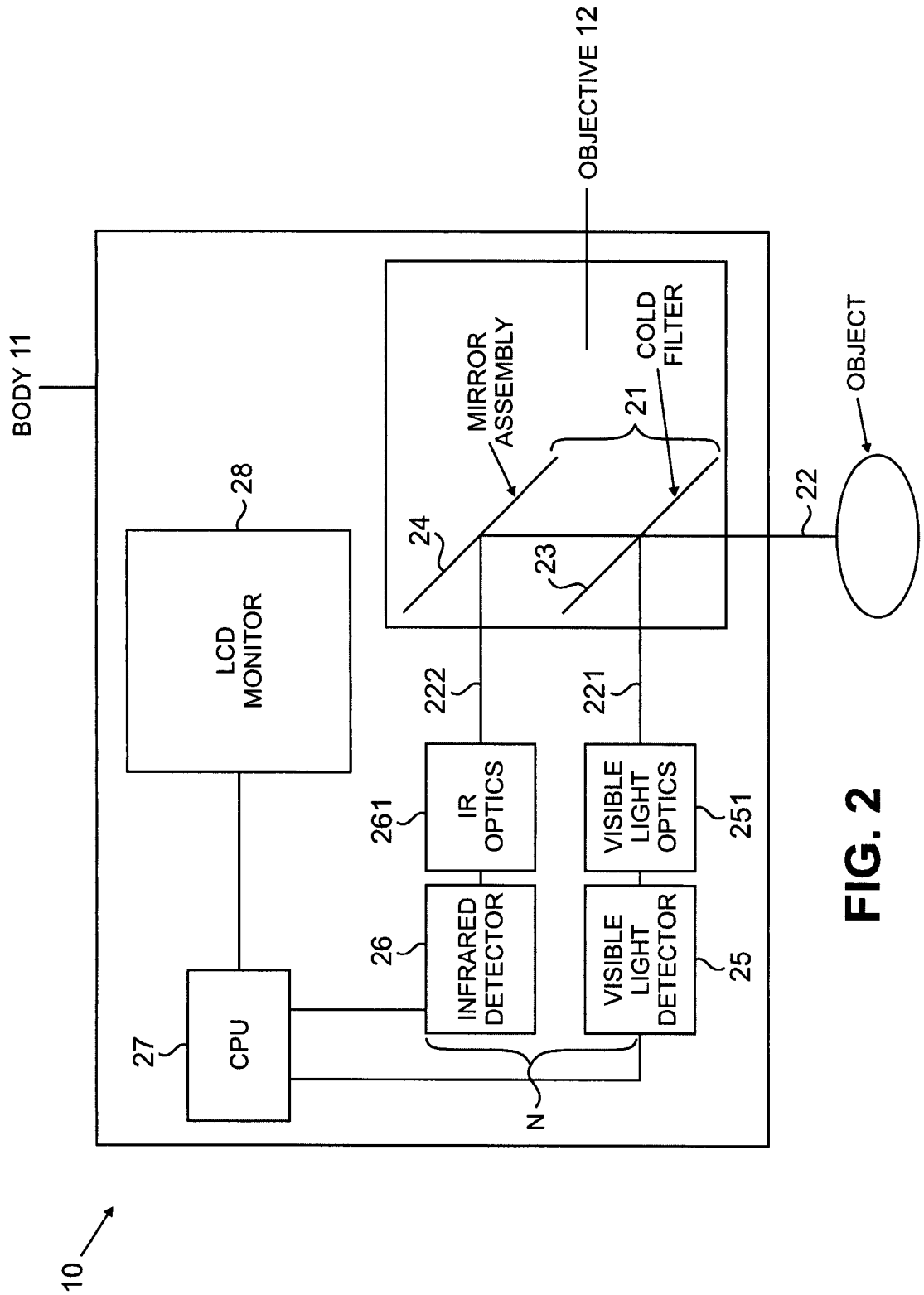
FIG. 2 illustrates the various components of the integrated multi-spectral imaging system shown in FIGS. 1A-B.

The objective portion 12, in one embodiment, may be designed to be positioned over a target or object 14, e.g. tissue or organ, to be monitored and/or imaged. The objective portion 12 may include an opening 15 through which a photon beam 16 emitted from object 14 may be directed into the objective portion 12. Looking now at FIG. 2, the multi-spectral imaging system 10 may include within the objective portion 12 an assembly 21 for separating or splitting photon beam 22 into multiple incident rays, each within a different wavelength spectrum. As illustrated in FIG. 2, assembly 21 may be designed to separate photon beam 22 into at least two incident rays 221 and 222 of different wavelengths. To accomplish this, assembly 21 may be provided, in one embodiment, with an array of at least two mirrors 23 and 24. In accordance with one embodiment of the present invention, mirror 23 may be designed to reflect an incident ray 221 having photons within a specific wavelength spectrum, for instance, visible light spectrum, while being transparent to photons within different wavelength spectra, for instance, near-, mid-, and far-infrared. Mirror 23, accordingly, may be made from germanium, or any material that may be reflective of photons within the visible spectrum, while being transparent to photons within the infrared spectrum. Mirror 24, on the other hand, may be designed to reflect an incident ray 222 having photons within a specific infrared spectrum, e.g., mid-infrared (8-10 µm). In one embodiment, mirror 24 may be made from glass, stainless steel, chromium, or any material that may be reflective of photons within the mid-infrared spectrum.

Although only two mirrors are illustrated in FIG. 2, it should be appreciated that additional mirrors may be provided, with each mirror in the array being designed to reflect photons within a specific wavelength spectrum, while being transparent to those in other wavelength spectra. The number of mirrors used in the array and the wavelength spectra at which these mirrors may reflect can be dependent on the tissue characteristics to be monitored and the image or images to be generated. Accordingly, should an optical image not be necessary for the particular application, the mirrors provided may, for example, be reflective only to photons within the various infrared spectra. Moreover, should it be desired, the mirrors in the array may be designed to reflect incident rays having photons within various other wavelength regions of the electromagnetic spectrum, e.g., x-rays, ultraviolet etc., depending on the imaging application.

In an alternate embodiment, assembly 21 may include, instead of an array of mirrors, a plurality of filters, shutters, hot/cold prisms, or a combination thereof, each similarly capable of separating and/or reflecting photons within a specific wavelength spectrum while being transparent to photons within other wavelength spectra. Furthermore, to the extent necessary, these mirrors, filters, shutters, and/or hot/cold prisms may be fixed or made to be adjustable in order to vary the angle of incidence.

Still referring to FIG. 2, the multi-spectral imaging system 10 may also be provided with a detection network N. In the embodiment shown in FIG. 2, detection network N includes detectors 25 and 26 positioned within the body portion 11 to collect incident rays 221 and 222 respectively. Since incident rays 221 and 222, reflecting off of mirrors 23 and 24 respectively, are of different wavelength spectra, each of detectors 25 and 26 may be tuned to the specific wavelength spectrum for the incident ray it is collecting. In the embodiment illustrated in FIG. 2, detector 25 may be tuned to collect photons in the visible light spectrum, while detector 26 may be tuned to collect photons in the infrared spectrum, for example, mid-infrared spectrum (i.e., 8-10 $\mu$m). Detectors 25 and 26, in one embodiment of the invention, may be single-band (i.e., single-spectrum) detectors that are commercially available. Alternatively, infrared detector 26 may be a multi-band (i.e., multi-spectral) detector, capable of receiving photons within various infrared spectra. In other words, should the specific wavelength spectrum of an incident ray to be collected changes from one application to another, detector 26 may still be capable of collecting such an incident ray, should the incident ray comprises photons within the spectra of wavelengths to which the detector 26 may be tuned. In one embodiment, multi-band detector 26 may be a quantum well infrared photodetector (QWIP), such as those disclosed in U.S. Pat. Nos. 5,539,206, 6,184,538, 6,211,529, and 6,642,537, all of which are hereby incorporated herein by reference.

To collect the respective incident rays reflecting off of mirrors 23 and 24, a substantially clear pathway may be provided between the mirrors and detectors 25 and 26. In particular, an opening (not shown) may be provided at a juncture between the body portion 11 and the objective portion 12 that is sufficiently large to permit the incident rays 221 and 222 to move substantially unobstructively therethrough. In one embodiment of the invention, optics components, such as lens 251 and 261 may each be positioned upstream of detectors 25 and 26 respectively to permit the corresponding incident ray to be focused onto the respective detector. In addition, in accordance with an embodiment of the present invention, detectors 25 and 26 may be situated in such a manner so as to allow incident rays 221 and 222 to arrive at the respective detectors substantially perpendicularly to the surface of the detectors. To accommodate this, mirrors 23 and 24 may be fixed at an appropriate angle relative to the detectors 25 and 26, or may be adjustable to vary the angle of incidence.

In general, detectors 25 and 26 may be designed to correlate functional, physical and/or optical data from incident rays 221 and 222 coming from the same spatial and temporal source, i.e., object 14. It should be noted that since the correlated data came from photon beam 22 for all wavelength frequencies, any distortion that might be derived from the beams transmitted at different angles from object 14 may be minimized. In addition to correlating data, detectors 25 and 26 may be designed to convert the correlated data from the respective incident rays 221 and 222 into electronic signals.

Figure 3:
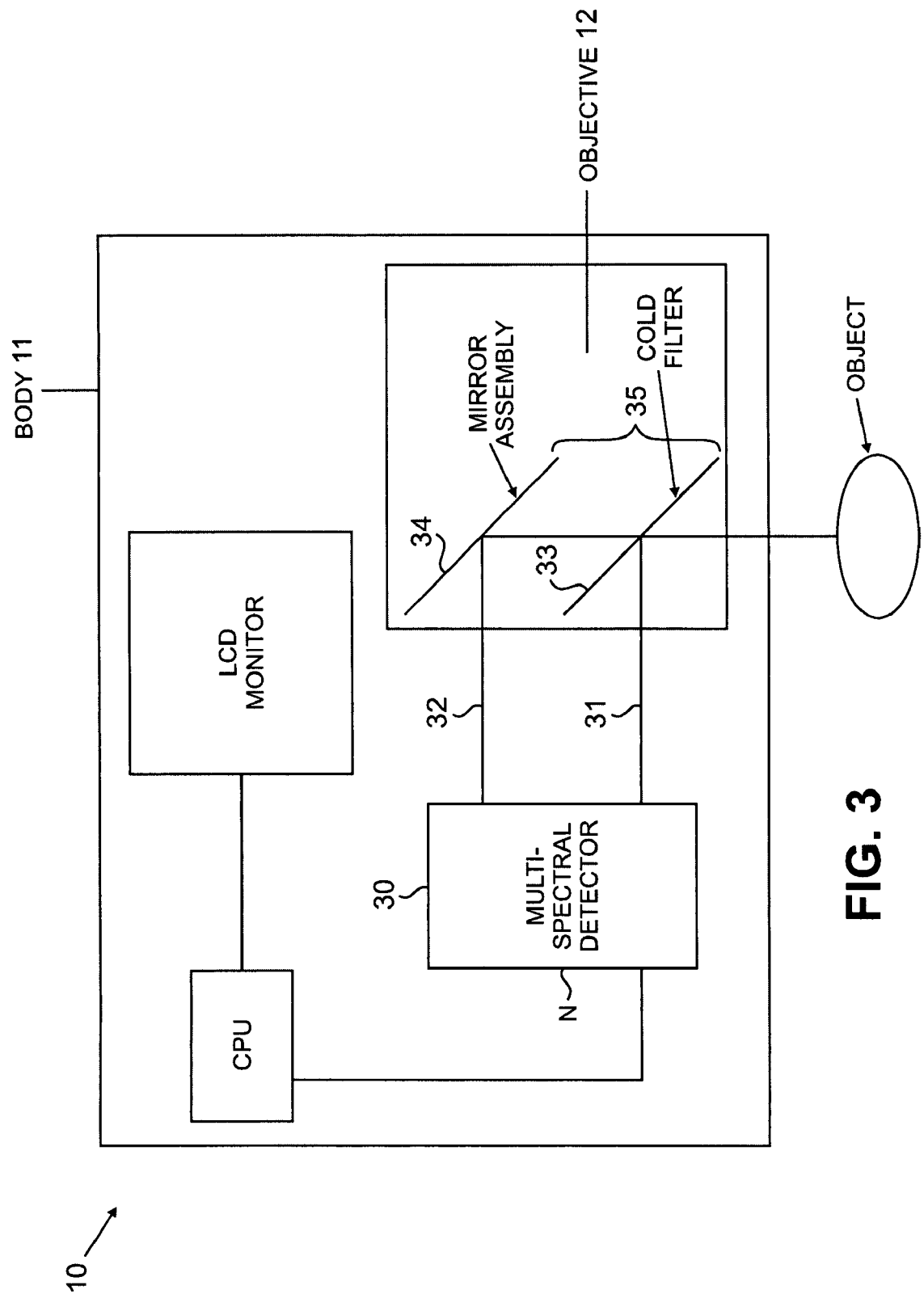
FIG. 3 illustrates an alternate embodiment for the detection component of the integrated multi-spectral imaging system shown in FIGS. 1A-B.

It should be appreciated that although FIG. 2 illustrates a network N of two detectors, additional detectors may be provided within network N depending on the number of incident rays that may be generated from the beam separator assembly 21. Alternatively, the multi-spectral imaging system 10 may employ only one detector 30 in network N, as shown in FIG. 3. In such an embodiment, the detector 30 may preferably be a multi-spectral detector, for instance, a QWIP multi-spectral detector as noted above. The use of a multi-spectral detector 30 may permit multiple incident rays, such as rays 31 and 32, each of which comprises a different wavelength spectrum, to be received by the multi-spectral detector 30 for data correlation regarding the object being monitored. To direct these various incident rays on to detector 30, mirrors 33 and 34 of beam splitting assembly 35 may be made adjustable to alter the angle of incidence. Should it be desired, additional reflectors (not shown) may be positioned between each mirror and the detector 30 to adjust the angle at which each incident ray may be received by the detector 30. In particular, the additional reflectors may redirect the pathway of each incident ray to arrive at the detector 30 substantially perpendicularly.

Referring again now to FIG. 2, the integrated multi-spectral imaging system 10 may further include a processor 27. Processor 27, in one embodiment, may be designed to receive, as electronic signals, the correlated data from detectors 25 and 26, and to generate, in real time, discrete physical and/or functional data as well as image data regarding the object from the electronic signals using a variety of processing options and capabilities. Such a processor may be similar to those disclosed in U.S. Pat. Nos. 5,810,010, 5,961,466, and 5,999,843, all of which are hereby incorporated herein by reference. For example, processor 27 may be provided with a variety of algorithms so that it may generate, from the infrared data, (i) real time information relating to, for example, blood perfusion, tissue characteristics, minute temperature changes, presence of tumorous growth or abnormal tissue behavior, as well as (ii) functional or physiological image signals of such information in connection with the object or target being monitored and/or observed. Data from the visible spectrum, on the other hand, may be used to generate optical image signals of the object or target being observed. The functional/physiological image signals and the optical image signals may be manipulated by processor 27, through a variety of user input, for subsequent display as either a discrete functional image (i.e., from the infrared spectrum) and a discrete optical image (i.e., from the visible spectrum), or as an integrated multi-spectral image of the object being monitored and observed. The integrated multi-spectral image, in accordance with an embodiment, may be a superimposition of a functional image onto an optical image. In this manner, the integrated image can allow a tending physician to visualize, for example, the functional and physical behavior and/or characteristics within the object (e.g., tissue or organ) being monitored and observed.

In one embodiment of the present invention, processor 27 may be positioned internally within the body portion 11 of the integrated multi-spectral imaging system 10, as illustrated in FIG. 2. Alternatively, processor 27 may be positioned externally of the body portion 11 and remotely from the integrated multi-spectral imaging system 10. Whether the processor 27 is within or outside of the body portion 11, electronic signals from the detectors 25 and 26 may be transmitted to the processor 27, in an embodiment, via wires. In an alternate embodiment, where the processor 27 is positioned remotely from the multi-spectral imaging system 10, electronic signals from the detectors 25 and 26 may be transmitted wirelessly to processor 27.

To permit visualization of the image signals generated by the processor 27, the integrated multi-spectral imaging system 10 of the present invention may be provided with a display system, such as screen 28, located at the output display portion 13 of the imaging system 10. In one embodiment, the display system may include screens 28 positioned atop the body portion 11 and pivotally connected thereto (See FIGS. 1A-B). The pivotal connection of the screens 28 to the body portion 11 allows the screens 28 to be moved into a substantially upright position, as shown in FIGS. 1A-B, for viewing, or folded substantially flush against the body portion 11 when not in use. It should be appreciated that the display system of the present invention may include two or more screens 28 to permit multiple users, for example, a tending physician and an assistant, to comfortably view the images being displayed thereon. However, it can be well envisioned that only one screen may be provided. Should it be desired, screens 28 may also be designed to rotate circumferentially atop the body portion 11, so that a user may avoid having to relocate his/her position when relocation may be difficult. Screens 28, in one embodiment, may be commercially available LCD screens, or any other display device capable displaying images for viewing by the user. Screens 28 of the display system may also be provided remotely (not shown) from the body portion 11. In such an embodiment, the remotely available screens 28 may be used in substitution or in addition to the screens on the body portion 11.

Figure 4:
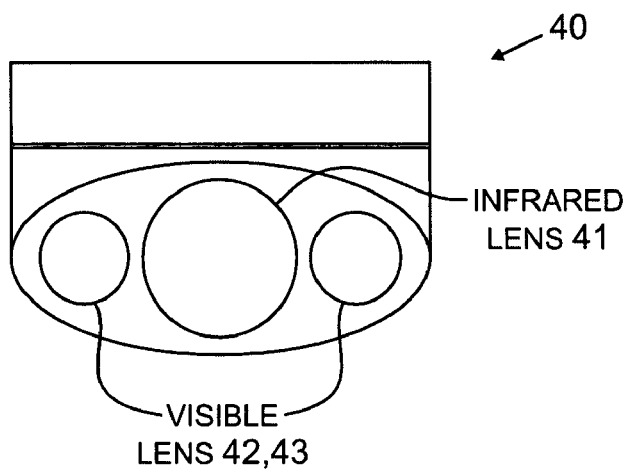
FIG. 4 illustrates an end view of a lens system for use in connection with the integrated multi-spectral imaging system shown in FIGS. 1A-B.
Figure 5:
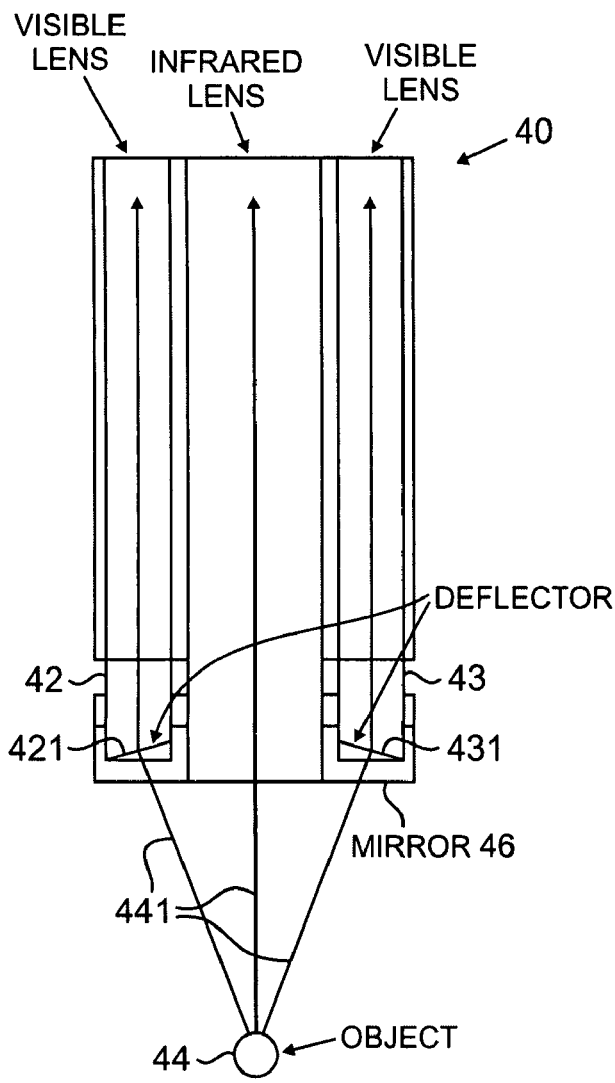
FIG. 5 illustrates a longitudinal section view of the lens system in FIG. 4.

Looking now to FIGS. 4 and 5, in one embodiment of the present invention, the integrated multi-spectral imaging system 10 may be equipped with lens system 40 for generating, among other things, binocular or three dimensional (3-D) images of the object being monitored and observed. Lens system 40, in an embodiment, may be coupled to the opening 15 of the objective portion 12, shown in FIGS. 1A-B, and may include at least three lenses, for instance, a center lens 41, and side lenses 42 and 43. The center lens 41 and side lenses 42 and 43 may be situated so as to be directed at the same focal point of an object 44 being observed. The center lens 41, in an embodiment, may be an infrared lens, and may be positioned over the object 44 to collect photon beam 441 emitted therefrom. Side lenses 42 and 43, in one embodiment, may be visible light lenses, and may be positioned so that each side lens can also be directed at the same focal point to which the center lens 41 may be focused. To permit the side lenses 42 and 43 to be focused at the same focal point as that by the center lens 41, deflectors 421 and 431 may be used to capture photon beams 442 and 443 from the object 44 and redirect these beams in the manner shown by arrows 422 and 432. Deflectors 421 and 431, in on embodiment, may be adjustable to permit the side lenses 42 and 43 to capture photon beams from the same focal point, taking into account the distance at which the side lenses 42 and 43 may be placed from the object 44.

It should be noted that although the lenses 41, 42 and 43 are illustrated as separate confocal lenses, each with the ability to focus on a similar focal point concurrently as the others, these lenses may not necessarily be separate or discrete in design. Instead, they may be configured to be integral with one another. In addition, more than three lenses may be used. Regardless of the configuration or design, and depending on the imaging application, the lens system 40 may be made to collect photon beams within various other wavelength regions of the electromagnetic spectrum, e.g., x-rays, ultraviolet, etc.

Figure 6:
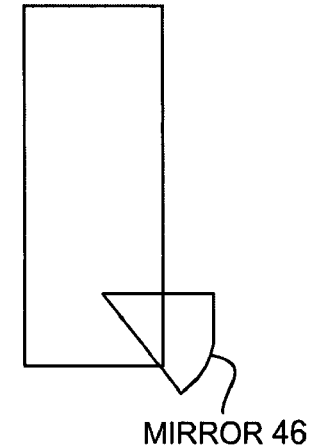
FIG. 6 illustrates a detailed view of a mirror in the lens system in FIG. 4.

The lens system 40, as illustrated in FIGS. 5 and 6, may also include, in one embodiment, a mirror assembly 46 positioned adjacent to the deflectors 421 and 431. The mirror assembly 46, in an embodiment of the invention, may be hingedly connected to the lens system 40 adjacent to the deflectors 421 and 431, so that the view by lenses 41, 42 and 43 may be adjusted to any angle from the normal incident.

The lens system 40, when positioned over object 44, may collect photon beams through each of the center lens 41 and side lenses 42 and 43. These beams, in accordance with an embodiment, may be directed as incident rays to three separate detectors similar to those detectors in FIG. 2. In particular, each of these detectors may be tuned to the specific wavelength spectrum of the incident ray it is receiving. The electronic signals generated by the detectors from the correlated data from the respective incident rays can then be transmitted to a processor similar to that shown in FIG. 2 for processing into respective functional and optical image signals. The functional and image signals may thereafter be manipulated and displayed either as separate (i.e., single spectrum) or merged (i.e., multi-spectral) 2D and/or 3D images.

In accordance with one embodiment of the present invention, the lens system 40 may be employed without the utilization of a beam splitting assembly, for example, assembly 21 in FIG. 2. However, such an assembly may still be used should the photon beam collected through, for instance, the infrared lens, needs to be separated into various specific infrared spectra, e.g., near-, mid-, and/or far-infrared.

The lens system 40 may also be equipped with a focus or zoom component. In this manner, a user may be able to, among other things, view functional and optical images of small regions of interest with greater control, including the ability to control the presentation of the field of view, to study the subject tissue at normal and at magnified settings, to obtain a substantially clear and focused image at varying magnification or distance, and to obtain a field of depth which can facilitate eye hand coordination, while performing the surgical procedure. It should be appreciated that the use of multiple discrete lenses in lens system 40 can minimize issues typically associated with image degradation when approaching from a single lens solution.

Figure 7A:
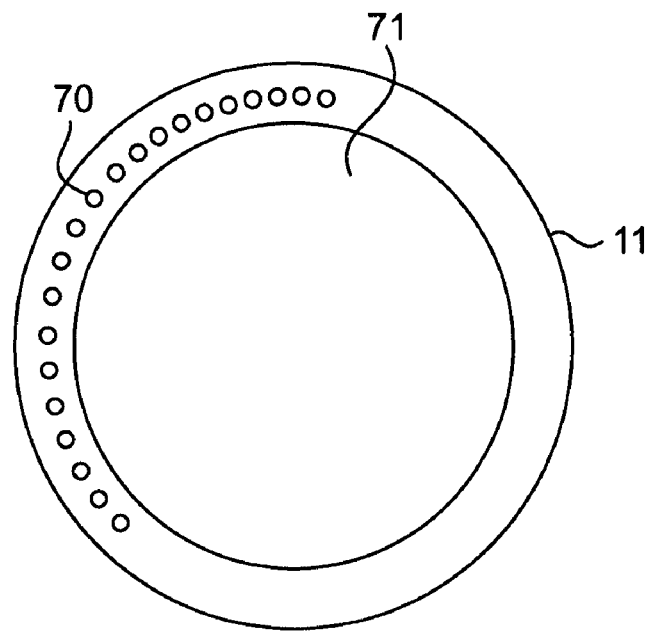
FIGS. 7A-B illustrate a various embodiments for a light source for use in connection with the integrated multi-spectral imaging system of the present invention.
Figure 7B:
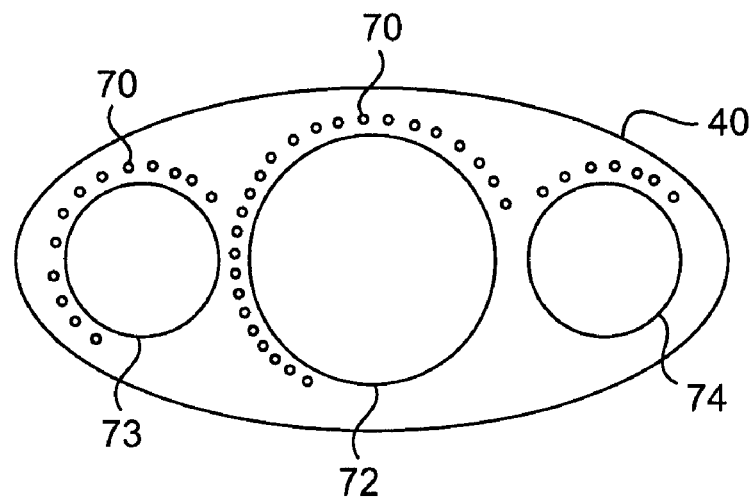

In another embodiment of the present invention, the integrated multi-spectral imaging system 10 may be equipped with one or more light sources for illuminating the object being monitored and viewed. As illustrated in FIGS. 7A-B, light source 70 may be situated, in one embodiment, about the opening 71 of the objective portion 11. In an embodiment whereby lens system 40 may be used, light source 70 may be situated about center lens 72 and/or side lenses 73 and 74. Light source 70, in accordance with one embodiment, may be a fiber optic light source, or any source which may generate diffuse illumination at the appropriate frequency on to the object being monitored and observed. The presence of light source 70, in one embodiment, can enhance the quality of the image data either by providing additional illumination and/or through spectral analysis, fluorescence or other means.

Figure 8:
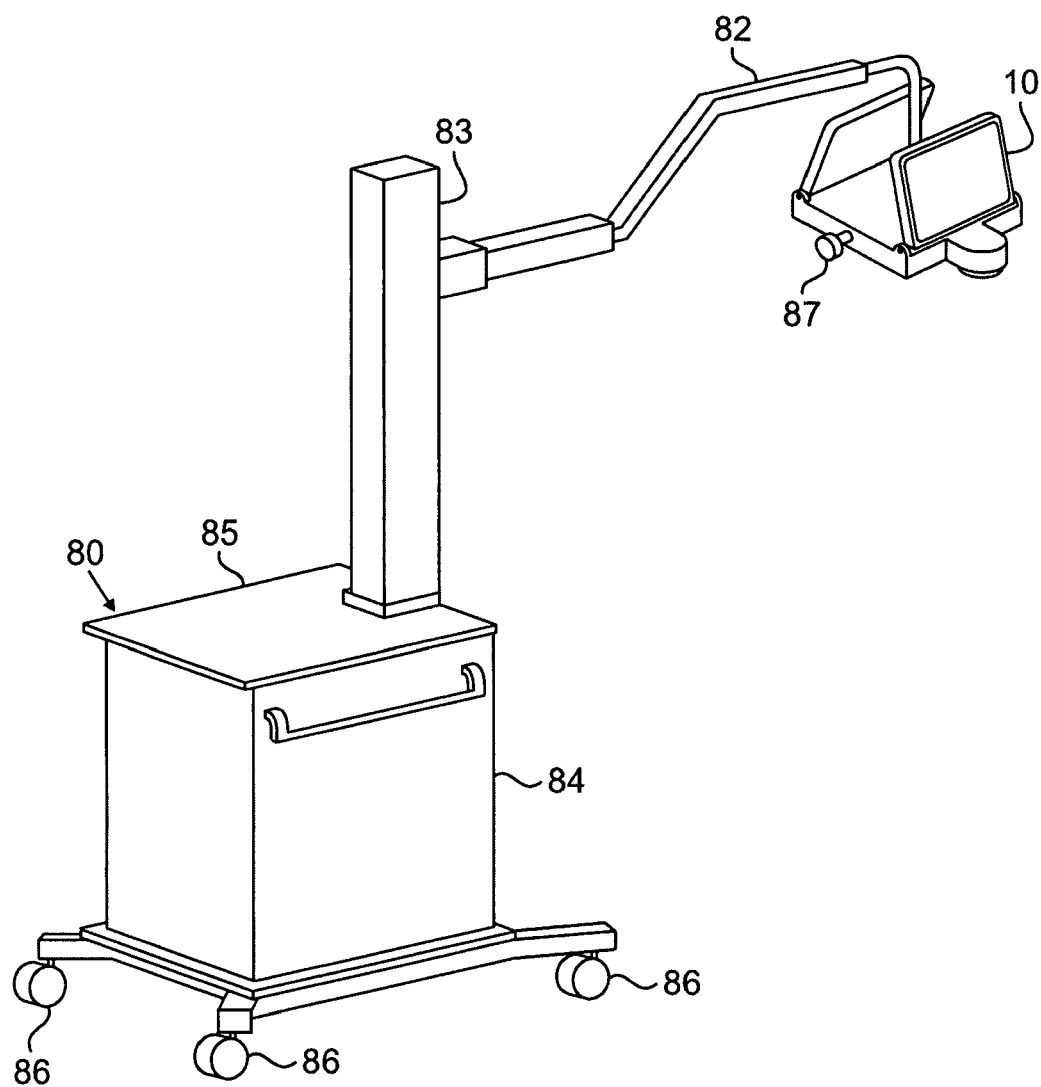
FIG. 8 illustrates a perspective view of an integrated multi-spectral imaging system of the present invention coupled to a scanner system for use in tissue analysis.

As illustrated in FIG. 8, the multi-spectral imaging system 10 of the present invention may be utilized in connection with a mobile cart 80 for ease of use. The cart 80, in one embodiment, may include a positioning arm 82 to which the multi-spectral imaging system 10 may be attached. The cart 80 may also include a stand 83 to which the arm 82 may be secured. The cart 80 may further include a housing 84 to which the stand 83 may be rigidly mounted. The housing 84, in an embodiment, may include multiple shelves (not shown) below surface 85, and on which, for instance, a power supply to the system 10, an external processor, and various other components and controller may be placed. As the system 10 may need to be moved for positioning over the object to be monitored and observed, the cart 80 may include wheels 86 to facilitate the relocation. In addition, system 10 may be provided with handle 87 to adjust the angle of positioning of the system 10 over the object being monitored and/or observed.

The integrated multi-spectral imaging system 10 of the present invention may be adapted for a variety of uses. In one embodiment, the integrated multi-spectral imaging system 10 can be used to obtain relatively fast and accurate images of the object being monitored and observed. Moreover, since the imaging protocol employed by the system 10 can be based on the registration of passively emitted infrared photon flux from the tissue, the system 10 requires essentially no physical contact with the tissue or organ being monitored or observed, thereby substantially eliminating the need for the use and delivery of contrasting agents into the tissue or organ.

In addition, the integrated multi-spectral system 10 of the present invention can be used in a non-invasive manner to monitor, for instance, the physiological, functional, and/or structural characteristics of the tissue or organ being observed by analyzing the infrared energy that is emitted, absorbed or reflected from the tissue or organ. Specifically, a multi-spectral detector or detectors may be used to collect, for example, infrared data from two or more bands and the intensity of each of the bands thereafter may be compared to determine tissue characteristics.

In particular, infrared photons, or "black body radiation", emitted from the tissue and organ being monitored and observed may be collected as a stream of individual frames by the multi-spectral detector. Subsequently, each frame may be analyzed and compared for changes in the photon flux. Changes in photon flux are typically the direct results of changes in tissue physiology. In one example, the multi-spectral system 10 may be used to identify/determine, among other things, an area of low blood flow in, for example, heart tissue, by comparing the intensity of the infrared flux at the absorption band of $CO_2$, about 3 to 5 $\mu$m, versus the absorption band of oxygenated hemoglobin, from about 0.1 to 2 $\mu$m, and preferably about 0.6 $\mu$m to 1.0 $\mu$m, or to any other band. This information could assist a heart surgeon in locating the optimal point for a bypass graft.

Moreover, as there can be many biomedical applications which may require the ability to determine the concentration of naturally occurring or introduced chemicals in living tissue, the integrated multi-spectral system 10 of the present invention may be used to measure, for instance, oxygen and/or $CO_2$ concentration to assist clinicians in assessing disease state and response to therapy. The ability to detect and measure, in vivo and in real time, concentrations of naturally occuring or introduced chemicals or gases in tissue or organs permit, in one embodiment, segmentations of data as a function of depth in tissue by comparing at least two frequencies that have different depth penetration capabilities, for example, about 3-5 $\mu$m vs. about 8-10 $\mu$m. The multi-spectral system 10 of the present invention, as should be noted, can be adapted to generate 3-D infrared data sets, which can further enhance this ability. In addition, detectors, including multi-spectral detectors, can be customized to track specific pharmacological substance introduced into tissue or be tuned to certain chemical by-products of disease, such as cancerous production of NO.

The integrated multi-spectral imaging system 10 may also be used in pre-operative evaluation, for example, in the evaluation of the vascular architecture and more specifically, the perforator vessels. The ability to evaluate the vascular architecture can assist in the subsequent harvesting of a tissue flap, the assessment of the effects of diseases, such as cancer and diabetes, and the evaluation of vascular functional behavior using DAT, including non-infrared methods capable of monitoring changes in perfusion periodicity.

To perform a pre-operative evaluation of the vascular architecture, in one embodiment, the objective portion of system 10 may be placed over of the area being evaluated. Next, a mark may be made on the body part using a surgical marker within the field of view of the imaging system 10. The mark, in accordance with an embodiment of the present invention, can be used as a reference of a coordinate system. Once the mark has been made, the imaging system 10 may be activated to scan the area being evaluated. The scan, in one embodiment, may be about 20 seconds in length, but can vary in length of time, depending on the procedure. The system 10 may then process the data captured from the scan using one and/or all of the following algorithms: Spot FFT (Fast Fourier Transformation), Spot Corrections FFT, Spot Standard Deviation FFT, Spot Average, Spot Slope, Spot Standard Deviation, Spot Average Correction, Spot Standard Deviation Series. The results of scanned data processing may thereafter be presented as an image or images on the display screen of the imaging system 10. The image or images presented on the display screen, in one embodiment, may be pseudo-color or color images for evaluation. An operator may subsequently, if desired, manipulate the imaging system 10, including for example, selecting and narrowing different parameters, such as frequency and/or temperature range, to further enhance the contrast between, for instance, the perforator vessels (i.e., those vessels comprising the vascular architecture) and surrounding tissue to show the distribution and location of perforator vessels. It should be appreciated that the localization of the perforator vessels may be carried out by the imaging system 10 with a resolution of approximately ±2 mm.

The integrated multi-spectral imaging system 10 of the present invention may further be used pre-operatively, for instance, to stage the advancement of a disease and its effect on perfusion, such as in the case of diabetic neuropathy, or to plan a surgical procedure in response to the pre-operative result by identifying the best method and location for intervention. The imaging system 10 may also be used to evaluate perfusion in organs to be used during the transplantation, and may have applications in monitoring changes in perfusion related to patient behavior, such as exercise and diet, for instance, in the case of diabetic neuropathy. In such a situation, the imaging system 10 may provide important screening or diagnostic information, so as to identify the existence, stage the advancement, or monitor the effects of behavioral modifications, chemotherapy, surgical intervention or other medical or physical therapy over the lifetime of the patient.

The integrated multi-spectral imaging system 10 may also be used in connection with post-operative evaluation, for instance, blood perfusion within a tissue graft or transplanted organ. In one embodiment, the integrated multi-spectral imaging system 10 may initially be focused on the tissue or organ to be examined to evaluate blood perfusion during the post-operative period. Thereafter, operator may set parameters, for example, parameters similar to that in a sequential scanning protocol. This protocol, in one embodiment, allows the taking of a series of images over an extended period of time (seconds, minutes, hours, days etc.). The number of image frames, the total period of image collection, and the pause between consecutive collections can be set. The analysis of the collected images allows instant evaluation of the blood perfusion during the postoperative period.

In the same way, and for similar reasons, the integrated multi-spectral imaging system 10 of the present invention may be useful for post-operative monitoring of other surgical procedures including, but not limited to, rejoining of limbs following traumatic amputation, transplantation of organs or tissue, and interventional vascular procedures, such as angioplasty and stenting of vessels.

It should be noted that the design of the integrated multi-spectral imaging system 10 makes the system easily adaptable to various applications. For instance, the processor used in connection with the system 10 may be easily adapted for the particular application in use. Specifically, the type of application to be implemented can determine the type of algorithm that is to be used. For instance, whether the intention is to analyze massive changes of blood flow in major blood vessels, or minute changes in capillaries or cellular metabolic behavior, the system 10 can be easily adjusted and optimized by the user through an easy-to-use interface. Moreover, the configuration of the system 10 can lend itself to being used, for instance, in either a conventional wide-field surgery or alternately during minimally invasive surgery through the use of an endoscopic accessory lens.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims. It should be noted that although surgical procedures are suggested, the potential uses for system 10 is not limited to such, or for that matter, medical applications.

What is claimed is:

1. A multi-spectral imaging system comprising:
   an assembly for splitting a photon beam emitted from an object being monitored into multiple incident rays of different wavelength spectra;
   a plurality of detectors, each being tuned to a specific wavelength spectrum of the respective incident ray it is collecting, for converting, into electronic signals, data correlated from the respective incident ray and a lens situated upstream of each of the detectors to permit the corresponding incident ray to be focused on to the respective detector;
   a processor for generating discrete image data from the electronic signals of each respective incident ray for subsequent display as individual images, or as an integrated multi-spectral image; and
   a display for viewing the image data,
      further including a lens system through which photon beams within various wavelength spectra from an object being monitored may be directed for providing binocular or three dimensional images of the object.

2. An imaging system as set forth in claim 1, wherein the lens system includes a plurality of lenses, each being directed at a similar focal point on the object being monitored.

3. An imaging system as set forth in claim 2, wherein at least one of the lenses is designed to collect a photon beam within an infrared spectrum and at least one other lens is designed to collect a photon beam within a visible light spectrum.

4. A multi-spectral imaging system comprising:
   a lens system through which photon beams within various wavelength spectra and originating from a similar focal point on an object being monitored may he directed for providing binocular or three dimensional images of the object;
   a plurality of detectors, each being tuned to a specific wavelength spectrum of the respective incident ray it is collecting, for converting, into electronic signals, data correlated from the respective incident ray and a lens situated upstream of each of the detectors to permit the corresponding incident ray to be focused on to the respective detector;
   a processor for generating discrete image data from the electronic signals of each respective incident ray for subsequent display as individual images, each of a different wavelength spectrum, or as an integrated multi-spectral image; and a display for viewing the image data.

5. A imaging system as set forth in claim 4, wherein the lens system includes a plurality of lenses, each being directed at a similar focal point on the object being monitored.

6. An imaging system as set forth in claim 5, wherein at least one of the lenses is designed to collect a photon beam within an infrared spectrum and at least one other lens is designed to collect a photon beam within a visible light spectrum.

* * * * *

UNITED STATES PATENT AND TRADEMARK OFFICE
CERTIFICATE OF CORRECTION

PATENT NO. : 7,265,350 B2  
APPLICATION NO. : 11/070925  
DATED : September 4, 2007  
INVENTOR(S) : Mark A. Fauci Page 1 of 1

It is certified that error appears in the above-identified patent and that said Letters Patent is hereby corrected as shown below:

Col. 1, Line 63, after "solution", change "tend" to -- tends --.

Col. 2, Line 7, after "observed", change "can" to -- could --.

Col. 2, Line 8, after "spectra", change "can" to -- could --.

Col. 2, Line 45, after "system", insert -- may --.

Col. 3, Line 48, after "illustrate", delete "a".

Col. 4, Line 12, after "shape", change "so" to -- as --.

Col. 5, Line 22, after "collected", change "changes" to -- change --.

Col. 5, Line 27, after "a", delete "quantum well infrared photodetector".

Col. 5, Line 27, change "(QWIP)" to -- QWIP --.

Col. 7, Line 18, after "capable", insert -- of --.

Col. 8, Line 22, after "lens", change "needs" to -- need --.

Signed and Sealed this

Twenty Second Day of April, 2008

JON W. DUDAS  
*Director of the United States Patent and Trademark Office*